(12) United States Patent
Vaez-Iravani et al.

(10) Patent No.: US 8,283,631 B2
(45) Date of Patent: Oct. 9, 2012

(54) IN-SITU DIFFERENTIAL SPECTROSCOPY

(75) Inventors: Mehdi Vaez-Iravani, Los Gatos, CA (US); Mehran Nasser-Ghodsi, Hamilton, MA (US); Guoheng Zhao, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 445 days.

(21) Appl. No.: 12/351,215

(22) Filed: Jan. 9, 2009

(65) Prior Publication Data

US 2009/0278044 A1 Nov. 12, 2009

Related U.S. Application Data

(60) Provisional application No. 61/051,368, filed on May 8, 2008.

(51) Int. Cl.
*G01N 23/00* (2006.01)
*G21K 7/00* (2006.01)
*H01J 40/00* (2006.01)

(52) U.S. Cl. ......... 250/310; 250/305; 250/307; 250/306

(58) Field of Classification Search .................. 250/305, 250/306, 307, 310
See application file for complete search history.

(56) References Cited

U.S. PATENT DOCUMENTS

| 3,739,170 | A | * | 6/1973 | Bohn et al. | 250/305 |
|---|---|---|---|---|---|
| 3,760,180 | A | * | 9/1973 | Weber | 250/305 |
| 4,021,674 | A | * | 5/1977 | Koops | 250/492.2 |
| 4,034,220 | A | * | 7/1977 | le Gressus et al. | 250/305 |
| 4,134,014 | A | * | 1/1979 | Neave et al. | 250/305 |
| 4,162,492 | A | * | 7/1979 | Jones, Jr. | 345/15 |
| 4,164,640 | A | * | 8/1979 | Scheffels | 219/121.3 |
| 4,379,231 | A | * | 4/1983 | Shii et al. | 250/311 |
| 4,670,650 | A | * | 6/1987 | Matsuzawa et al. | 250/307 |
| 4,882,486 | A | * | 11/1989 | Kruit | 250/305 |
| 4,912,327 | A | * | 3/1990 | Waugh | 250/307 |
| RE33,275 | E | * | 7/1990 | Wardell et al. | 250/305 |
| 5,210,414 | A | * | 5/1993 | Wallace et al. | 250/307 |
| 5,231,287 | A | * | 7/1993 | Sekine et al. | 250/305 |
| 5,345,080 | A | * | 9/1994 | Yajima et al. | 250/311 |
| 5,877,496 | A | * | 3/1999 | Tabuse et al. | 250/288 |
| 6,214,408 | B1 | * | 4/2001 | Bahr et al. | 427/8 |

(Continued)

FOREIGN PATENT DOCUMENTS

JP 2001083111 A 3/2001

(Continued)

*Primary Examiner* — Robert Kim
*Assistant Examiner* — Brooke Purinton
(74) *Attorney, Agent, or Firm* — Luedeka Neely Group, P.C.

(57) ABSTRACT

A spectrometer having an electron beam generator for generating an electron beam that is directed at a sample. An electron beam positioner directs the electron beam onto a position of the sample, and thereby produces a secondary emitted stream from the sample, where the secondary emitted stream includes at least one of electrons and x-rays. An secondary emitted stream positioner positions the secondary emitted stream onto a detector array, which receives the secondary emitted stream and detects both the amounts and the received positions of the secondary emitted stream. A modulator modulates the electron beam that is directed onto the sample, and thereby sweeps the electron beam between a first position and a second position on the sample. An extractor is in signal communication with both the modulator and the detector array, and extracts a differential signal that represents a difference between the signals that are received from the first position and the signals that are received from the second position.

7 Claims, 2 Drawing Sheets

U.S. PATENT DOCUMENTS

| | | | |
|---|---|---|---|
| 6,465,781 B1 * | 10/2002 | Nishimura et al. | 250/306 |
| 6,495,841 B1 * | 12/2002 | Ando et al. | 250/492.23 |
| 6,855,926 B2 | 2/2005 | Palmer et al. | |
| 6,946,654 B2 * | 9/2005 | Gerlach et al. | 250/306 |
| 7,171,038 B2 * | 1/2007 | Adler et al. | 250/307 |
| 7,411,188 B2 * | 8/2008 | deCecco et al. | 250/305 |
| 7,456,399 B1 * | 11/2008 | Soderstrom | 250/305 |
| 7,560,691 B1 * | 7/2009 | Gubbens | 250/305 |
| 7,635,842 B2 * | 12/2009 | Nasser-Ghodsi et al. | 250/305 |
| 7,755,042 B1 * | 7/2010 | Toth et al. | 250/305 |
| 7,855,362 B1 * | 12/2010 | Brodie et al. | 250/305 |
| 2004/0021069 A1 | 2/2004 | Barnard | |
| 2004/0232327 A1 * | 11/2004 | Bateman et al. | 250/288 |
| 2007/0057666 A1 * | 3/2007 | Shimakura et al. | 324/212 |
| 2007/0096021 A1 * | 5/2007 | LeBlanc et al. | 250/282 |
| 2007/0176088 A1 * | 8/2007 | Li | 250/282 |

FOREIGN PATENT DOCUMENTS

| | | |
|---|---|---|
| JP | 2002214169 A | 7/2002 |

\* cited by examiner

IN-SITU DIFFERENTIAL SPECTROSCOPY

This application claims all rights and priority on U.S. provisional patent application Ser. No. 61/051,368 filed May 8, 2008. This invention relates to the field of integrated circuit fabrication. More particularly, this invention relates to using spectroscopy to inspect substrates.

FIELD

Background

Spectroscopy, such as Auger spectroscopy, is an important tool for material identification on the microscopic level in a variety of fields, including the fabrication process of integrated circuits. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

Traditional techniques for performing Auger spectroscopy involve taking sequential readings in an ultra-high vacuum environment. Another technique uses a massively parallel Auger spectroscopy system, which achieves a much faster result in a moderate vacuum environment.

However, both of these methods suffer from the problem of low contrast and vulnerability to background noise. This requires the acquisition of many averages, and paying special attention to positioning the beam on the exact area of interest.

What is needed, therefore, is a system that overcomes problems such as those described above, at least in part.

SUMMARY

The above and other needs are met by a spectrometer having an electron beam generator for generating an electron beam that is directed at a sample. An electron beam positioner directs the electron beam onto a position of the sample, and thereby produces a secondary emitted electron stream from the sample. An emitted electron stream positioner positions the emitted electron stream onto a detector array, which receives the emitted electron stream and detects both the amounts and the received positions of the emitted electron stream. A modulator modulates the electron beam that is directed onto the sample, and thereby sweeps the electron beam between a first position and a second position on the sample. An extractor is in signal communication with both the modulator and the detector, and extracts a differential signal that represents a difference between the signals that are received from the first position and the signals that are received from the second position.

By looking at differential signals, rather than absolute signals, the spectrometers according to the present invention are able to distinguish signal levels that are much lower than those of spectrometers that are constructed and operated in a traditional manner. Thus, readings can be taken in less time, for example, and other issues related to the cost of spectroscopy can be reduced or eliminated. In various embodiments, the spectrometer is either an Auger spectrometer or an EDX spectrometer.

According to another aspect of the invention there is described a spectrometer having an electron beam generator for generating an electron beam that is directed at a sample. An electron beam positioner directs the electron beam onto a position of the sample, and thereby produces a secondary emitted electron stream from the sample. An emitted electron stream positioner positions the emitted electron stream onto a detector array, which receives the emitted electron stream and detects both the amounts and the received positions of the emitted electron stream. A modulator modulates a voltage on the emitted electron stream positioner, and thereby sweeps the emitted electron stream across the detector. An extractor is in signal communication with both the modulator and the detector, and extracts a differential signal that represents trace constituents of the sample that differ from a background composition of the sample.

According to another aspect of the invention there is described a method for producing a differential spectrum, by directing an electron beam onto a sample and thereby producing a secondary emitted electron stream from the sample. The emitted electron stream is positioned onto a detector array that detects both the amounts and the received positions of the emitted electron stream. A modulator modulates at least one of (1) the directing of the electron beam onto the sample and (2) the positioning of the emitted electron stream onto the detector. Signal communication is provided between the modulator and the detector, and a differential signal is extracted, which represents a difference between signals generated by the at least one of the modulated electron beam and the modulated emitted electron stream.

The method can be implemented, for example, in an Auger spectrometer or an EDX spectrometer. In one embodiment, the modulator modulates the electron beam that is directed onto the sample, and thereby sweeps the electron beam between a first position and a second position on the sample, and the differential signal represents a difference between signals received from a first position on the sample and signals received from a second position on the sample. In another embodiment, the modulator modulates the emitted electron stream across the detector, and thereby sweeps the emitted electron stream across the detector, and the differential signal represents trace constituents of the sample that differ from a background composition of the sample.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

The embodiments described herein make possible the extraction of even minute traces of elements at a given position on sample. The present invention has at least two main embodiments (each with several subordinate embodiments), each of which generates what can be called a "differential" spectrum of the interrogated position on the sample. However, the term "differential" has somewhat different meanings as it is applied to the different embodiments.

Figure 1:
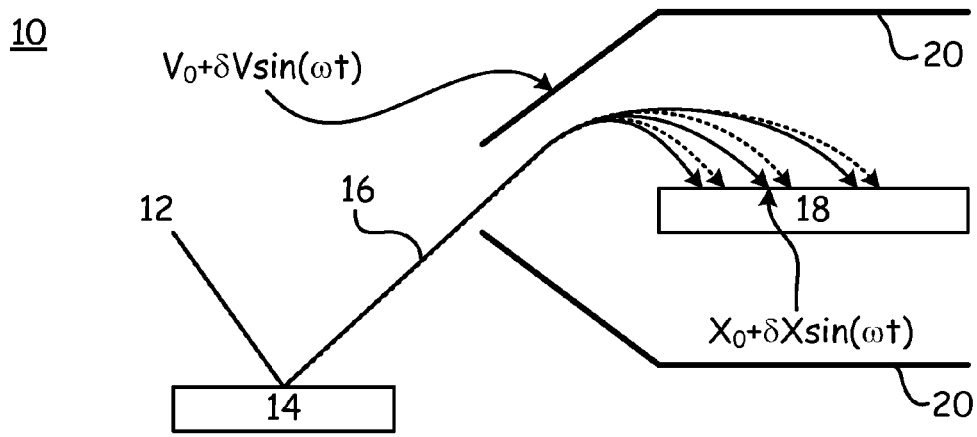
FIG. 1 is a graphical representation of a first embodiment of an Auger spectrometer according to the present invention, in which a voltage-varying method is employed.

In a first embodiment, "differential" indicates a difference in the constituents of a given interrogated position with respect to each other, such as d(NE)/d(E). This form of differential data is primarily a visualization aide, as it tends to enhance the subtleties in the spectrum. In this embodiment, as depicted in FIG. 1, the spectrometer 10 produces an electron beam 12 that is directed toward a sample 14, the collision of which produces Auger electrons 16. A sinusoidal voltage such as indicated is applied to the electrodes 20 of the collection system. The parallel detection system 18 allows the simultaneous detection of the Auger electrons over multiple channels. The application of this sinusoidal voltage means that the flight paths taken by the Auger electrons 16 undergo a certain level of sinusoidal wiggle, as indicated. The signal obtained at each element of the detector 18, therefore, is a combination of a "DC" signal, representing the background, and an "AC" component, which represents the differential value, d(NE)/d(E).

Figure 2:
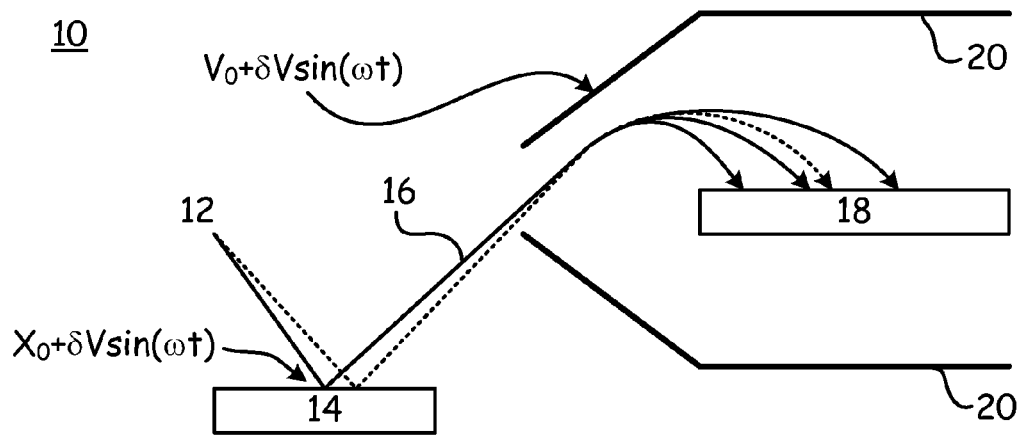
FIG. 2 is a graphical representation of a second embodiment of an Auger spectrometer according to the present invention, in which a position-varying method is employed.

In a second embodiment as depicted in FIG. 2, "differential" indicates a difference in the spectrum of a first position on the sample 14 with respect to that of a second position on the sample 14. In this embodiment, a small amplitude sinusoidal modulation signal is applied to the positioning electrodes of the electron beam 12, causing a sinusoidal wiggle in the beam 12, as indicated. The spectrometer 10 is not otherwise modified in this embodiment. Thus, the spectrometer 10 continues to analyze the Auger electrons as it typically would.

In this second embodiment, the resulting differential spectrum does not include any signal that is of equal amplitude for those elements that are present at both of the two positions, and only shows the differences in the elemental compositions at the two points on the sample 14. In other words, when the elemental contents of the two adjacent positions are identical, there are no elemental variations between the two streams of Auger electrons. In that case, regardless of where the electron beam 12 lands on the sample 14, the same Auger spectrum is generated.

Figure 3:
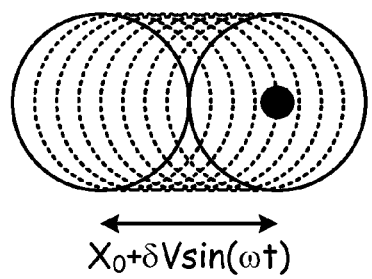
FIG. 3 is a graphical representation of the variation in position according to the second embodiment of the present invention.

FIG. 3 depicts the oscillation of the electron beam 12 back and forth between two points on the sample 14, where one of the positions includes a black spot, representing an elemental inclusion that is not present in the other position. When one position in the oscillation has a slight elemental variation from the other position on the sample 14, even though most of the elemental composition between the two positions is the same, then there exists a slight change in the Auger spectrum due to the elemental variation. Thus, the resulting Auger spectrum varies in a sinusoidal manner. By extracting the AC component of the Auger spectrum, even the smallest traces of the material of the dot can be extracted, to a level that is only limited by the electronic noise in the system 10.

Signal Extraction

For an Auger spectrometer with just a single element detector, the differential signal is simply the AC signal, which can be extracted by lock-in detection. However, this changes when dealing with an entire spectrum. Because the spectrum can be considered as a one-dimensional image, the signal can be extracted by using a technique that is similar to that used in lock-in thermography.

As mentioned above, the voltage applied to the electrodes 20 of the spectrometer 10, or the positioning electrodes of the electron beam 12, is modulated with a periodic signal, such as a sinusoidal function. Thus, the Auger spectrum that is generated is a sinusoidally varying spectrum. Multiple frames of the image, i.e. the spectrum generated in a parallel manner by the detector array, are acquired while the sample remains stationary. The images are then processed by applying a Fourier filter in a time domain at the frequency of modulation. The amplitude and phase images are given by:

$$S(x_i) = \frac{1}{N}\sum_{i=1}^{N} I_m(t_i)\sin\left(2\pi i\frac{f_1}{f_2}\right)$$

$$C(x_i) = \frac{1}{N}\sum_{i=1}^{N} I_m(t_i)\cos\left(2\pi i\frac{f_1}{f_2}\right)$$

$$t_i = \frac{1}{f_2}, i = 0, 1, 2, \ldots$$

$$x_i = mP, m = 1, 2, \ldots N_X$$

$$A = \sqrt{S^2 + C^2}$$

$$\Phi = \tan^{-1}\frac{S}{C}$$

Where $f_1$ is the frequency of the beam 12 position modulation (or voltage modulation of the electrodes 20) and $f_2$ is the frame rate. In some embodiments, $f_2$ is an even multiple of $f_1$. $X_i$ is the pixel position (or channel) in the detector array 18. N is the total number of frames that are captured, which in one embodiment is an integer multiple of the number of modulation cycles, which can be set to a desired number. A is the amplitude and $\Phi$ is the phase of the differential spectrum. The result thus obtained is a pure differential spectrum of either a point itself (a differential display), or a differential spectrum with respect to another adjacent point on the sample 14 (a material variation), depending on the mode of operation.

Figure 4:
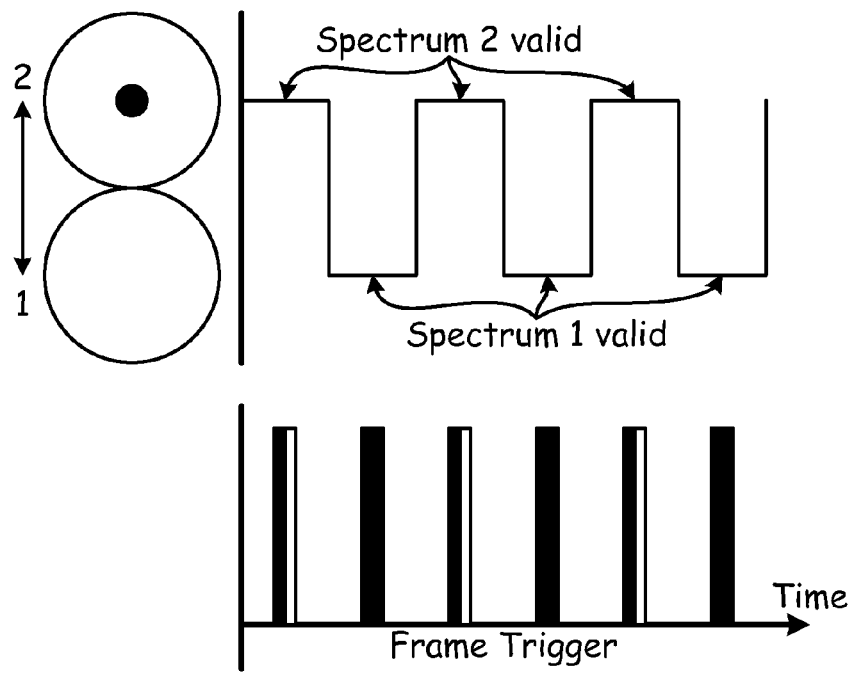
FIG. 4 is a graphical representation of the signals and frame triggers in the second embodiment of the present invention.
Figure 5:
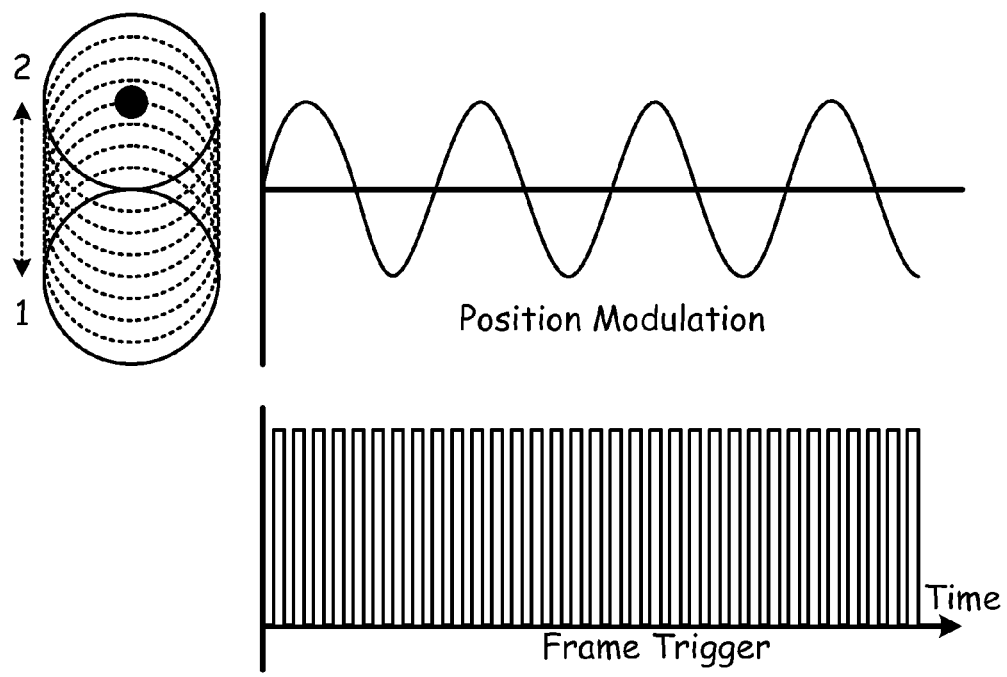
FIG. 5 is a graphical representation of the position modulation and frame triggers in the second embodiment of the present invention.

FIG. 4 depicts how the frame triggers can be used to select the signals that are generated by the two different spectrums. FIG. 5 depicts the modulation between the beam spot positions.

The technique described here allows one, for the first time, to have a complete differential spectrum of a particular position on the sample 14, particularly with respect to adjacent positions. It enables the isolation and identification of minute traces of a given material, in a manner only limited by the amount of electronic noise in the system 10. It allows for the complete cancellation of the background signals, such as "common mode/common element" signals.

This methodology can also be applied to other spectroscopic techniques, such as EDX. In the case of EDX, one detects the x-ray spectrum generated at the sample, which is characteristic of the constituent materials of the interrogated point. In generating a differential EDX spectrum, only the e-beam position modulation mode is applicable. The methodologies described herein are, in essence, general techniques to isolate variations between any two positions on a sample.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A spectrometer comprising:
   an electron beam generator for generating an electron beam that is directed at a sample,
   an electron beam positioner for directing the electron beam onto a position of the sample and thereby producing a secondary emitted stream from the sample,
   a secondary emitted stream positioner for positioning the secondary emitted stream onto a detector array,
   the detector array for receiving the secondary emitted stream and detecting both amounts and received positions of the secondary emitted stream, where the secondary emitted stream includes at least one of electrons and x-rays,
   a modulator for sinusoidally modulating at a frequency the position of electron beam that is directed onto the sample, and thereby repeatedly sweeping the electron beam between a first position and a second position on the sample, and
   an extractor in signal communication with both the modulator and the detector array, for extracting a differential signal by applying a Fourier filter in a time domain at the frequency of modulation, representing a difference between signal frames received from the first position during the repeated sweeps of the electron beam and signal frames received from the second position during the repeated sweeps of the electron beam.

2. The spectrometer of claim 1, wherein the spectrometer is an Auger spectrometer.

3. The spectrometer of claim 1, wherein the spectrometer is an EDX spectrometer.

4. A method for producing a differential spectrum, the method comprising the steps of:
   directing an electron beam onto a sample and thereby producing a secondary emitted stream from the sample, where the secondary emitted stream includes at least one of electrons and x-rays,
   positioning the secondary emitted stream onto a detector array,
   detecting both amounts and received positions of the secondary emitted stream with the detector array,
   with a modulator, sinusoidally modulating at a frequency at least one of the directing of the electron beam onto the sample and the positioning of the secondary emitted stream onto the detector array,
   providing signal communication between the modulator and the detector array, and
   extracting a differential signal by applying a Fourier filter in a time domain at the frequency of modulation, representing a difference between signal frames generated at different positions on the detector array by the at least one of the modulated electron beam and the modulated secondary emitted stream.

5. The method of claim 4, wherein the method is implemented in an Auger spectrometer.

6. The method of claim 4, wherein the method is implemented in an EDX spectrometer.

7. The method of claim 4, wherein the modulator modulates the electron beam that is directed onto the sample, and thereby sweeps the electron beam between a first position and a second position on the sample, and the differential signal represents a difference between signals received from a first position on the sample and signals received from a second position on the sample.

* * * * *